Aug. 25, 1964 E. S. BOERNER Plant Pat. 2,442
ROSE PLANT
Filed Oct. 16, 1963
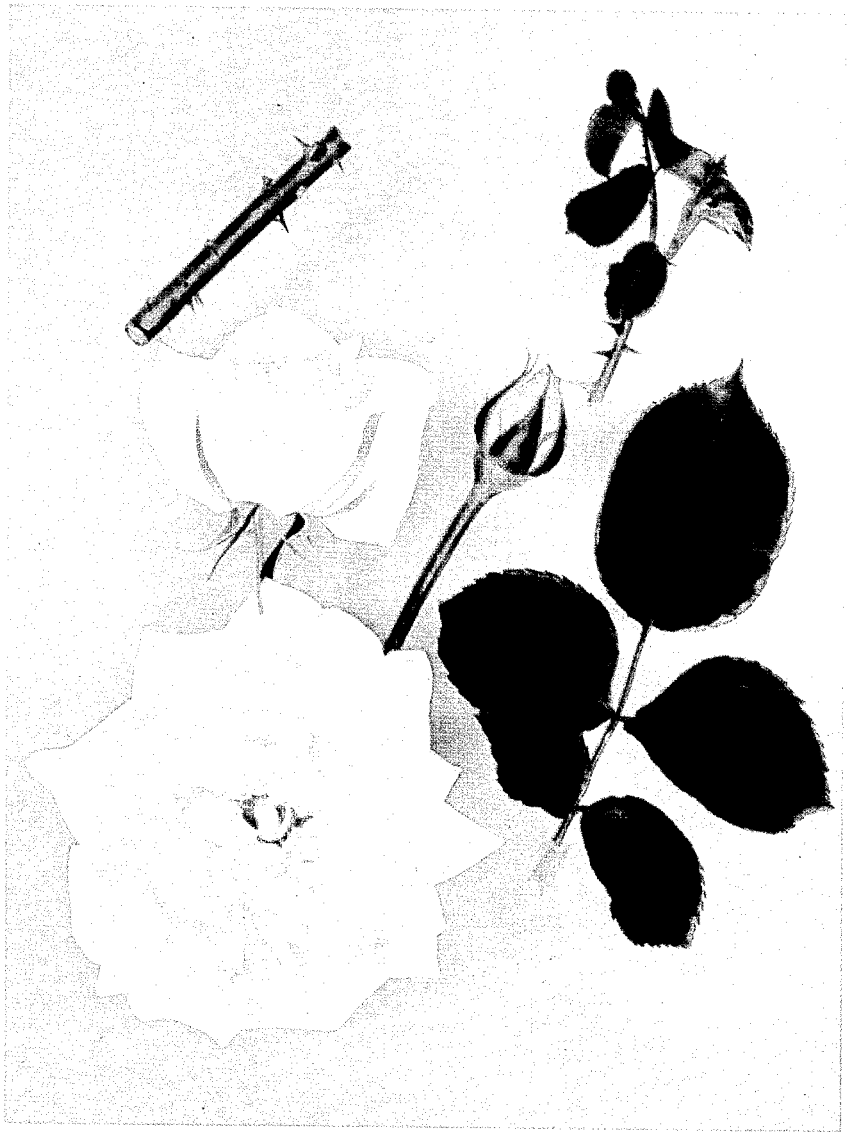
Inventor.
E. S. Boerner
By: Robb & Robb
Attorneys.

United States Patent Office

Plant Pat. 2,442
Patented Aug. 25, 1964

2,442
ROSE PLANT

Eugene S. Boerner, Newark, N.Y., assignor to Jackson & Perkins Company, Newark, N.Y., a corporation of New York Filed Oct. 16, 1963, Ser. No. 316,788
1 Claim. (Cl. Plt.—16)

The present invention relates to a new and distinct variety of rose plant of the hybrid tea class, which was originated by me by crossing an unnamed and unpatented seedling derived from a cross of "Diamond Jubilee" (Plant Patent No. 824) × "Kate Smith" (Plant Patent No. 1,317), with the variety known as "Tanya" (Plant Patent No. 1,712).

The primary object of this breeding was to produce a new and improved rose variety in which there is combined a stronger plant habit with the same general flower color as that of the parent variety "Tanya." This objective was fully achieved, along with other desirable features, as evidenced by the following unique combination of characteristics which are outstanding in the new variety and which distinguish it from its parents, as well as from all other varieties of which I am aware:

(1) A vigorous, strong and upright plant habit;

(2) A striking contrast between the color of the foliage and the color of the open flowers;

(3) Very distinctive and attractive flower buds which are highly colored and are predominantly Orange-Yellow, lightly overcast with Capucine-Orange; and (4) A distinctive, attractive and rich general color tonality of the open flowers corresponding to Apricot Yellow, lightly overcast with Deep Chrome.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetable growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—An unnamed seedling of "Diamond Jubilee" × "Kate Smith."
*Pollen parent.*—"Tanya."
Classification:
*Botanic.*—Hybrid tea.
*Commercial.*—Hybrid tea.

*Flower*

(Observations made from specimens grown outdoors at Newark, New York, near mid-morning during the latter part of the month of August.)

Blooming habit: Recurrent—continuous.
Bud:
*Size.*—Large.
*Form.*—Ovoid; is not affected by wet or hot weather.
*Color.*—When sepals first divide—Nopal Red, Plate 1. When petals begin to unfurl—Mikado Orange, Plate 3. When half-blown: inside of petals—Light Orange-Yellow, Plate 3, lightly overcast with Capucine-Orange, Plate 3; reverse of petals—Light Orange-Yellow, Plate 3, with outer edges overcast with Orange Chrome, Plate 2.
*Sepals.*—Slightly branched; curl back when petals begin to unfurl. Color: inside—Pale Olivine, Plate 32; outside—Absinthe Green, Plate 31, lightly overcast with Carmine, Plate 1.
*Calyx.*—Color—Biscay Green, Plate 17. Shape—funnel. Size—broad. Aspect—smooth. Odor when rubbed—none.
*Peduncle.* — Length—medium. Aspect—smooth. Strength—erect; heavy. Color—Brazil Red, Plate 1.
*Opening.*—Opens up well; is not affected by adverse weather conditions.
Bloom:
*Size.*—Large. Average size when fully expanded—5 inches.
*Borne.*—Singly.
*Stems.*—Medium length; strong.
*Form (when first open).*—Cupped. Permanence—retains its form to the end.
*Petalage.*—Double (full but open center). Number of petals under normal conditions—from 60 to 65.
*Color.*—Center of flower—Mikado Orange, Plate 3, lightly overcast with Orange-Buff, Plate 3. Outer petals—Pinard Yellow, Plate 4, with lower half of petals lightly overcast with Empire Yellow, Plate 4. Base of petals (aiglet)—Lemon Chrome, Plate 4. Inside of petals—Apricot Yellow, Plate 4, lightly overcast with Deep Chrome, Plate 3. Reverse of petals—Maize Yellow, Plate 4, very lightly overcast with Buff-Yellow, Plate 4. General tonality from a distance—Apricot Yellow, Plate 4, lightly overcast with Orange, Plate 3.
*Discoloration.*—General tonality at end of first day—Apricot Yellow, Plate 4, lightly overcast with Deep Chrome, Plate 3. Second day—Apricot Yellow, Plate 4, lightly overcast with Deep Chrome, Plate 3. Third day—Apricot Yellow, Plate 4, very lightly overcast with Deep Chrome, Plate 3.
Petals:
*Texture.*—Thick; is not affected by wet or hot weather.
*Appearance.*—Inside—satiny. Outside—shiny.
*Form.*—Oval.
*Arrangement.* — Imbricated (regularly arranged shingle-like).
*Petaloids in center.*—Many; large.
*Persistence.*—Drop off cleanly.
*Fragrance.*—Moderate. Nature—tea (average hybrid tea scent).
*Lasting quality.*—On plant—long. As cut flower—long.

*Genital Organs*

Stamens, anthers: Medium size; many; regularly arranged around styles. Color—Light Orange Yellow, Plate 3.
Stamens, filaments (threads): Medium length. Color—Empire Yellow, Plate 4.
Pollen: Color—Pale Yellow Orange, Plate 3.
Styles: Loosely separated; uneven length; medium length; thin.
Stigmas: Color—Scarlet, Plate 1.
Ovaries: All enclosed in calyx.
Hips: None.
Seeds: None.
Form: Bush.
Growth: Vigorous; upright.
Foliage: Compound of 5–7 leaflets.
*Size.*—Medium.
*Quantity.*—Normal.
*Color.*—New foliage: upper side—Victoria Lake, Plate 1; under side—Garnet Brown, Plate 1. Old foliage: upper side—Forest Green, Plate 17; under side—Light Bice Green, Plate 17.
*Shape.*—Oval pointed.

*Texture.* — Upper side—leathery. Under side—smooth.

*Ribs and veins.*—Ordinary.

*Edge.*—Serrated (saw-toothed).

*Serration.*—Both double and single; small.

*Leaf stem.*—Color—Brick Red, Plate 13. Under side—Prickly.

*Stipules.*—Medium length; bearded.

Wood:

*New wood.*—Color—Yellowish Oil Green, Plate 5. Bark—smooth.

*Old wood.* — Color—Varley's Green Plate 18. Bark—smooth.

Thorns:

*Thorns.*—Quantity: on main stalks from base—ordinary; on laterals from stalk—many. Form—narrow base; medium length; hooked downward. Color (when young)—Acajou Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a vigorous, strong, and upright plant habit, a striking contrast between the color of the foliage and the color of the open flowers, very distinctive, attractive and highly colored buds which are basically Light Orange Yellow, lightly overcast with Capucine-Orange, and a distinctive, attractive and rich general color tonality of the open flowers corresponding to Apricot Yellow, lightly overcast with Deep Chrome.

No references cited.